US006284955B1

US006284955B1

(12) United States Patent
Marshall et al.

(10) Patent No.: US 6,284,955 B1
(45) Date of Patent: Sep. 4, 2001

(54) CORN HYBRID P724

(75) Inventors: Lorelei C. Marshall, Iowa City; Terry J. Foley, Williamsburg, both of IA (US)

(73) Assignee: Optimum Quality Grains, LLC, Johnston, IA (US)

( * ) Notice: Subject to any disclaimer, the term of this patent is extended or adjusted under 35 U.S.C. 154(b) by 0 days.

(21) Appl. No.: 09/452,544

(22) Filed: Dec. 1, 1999

(51) Int. Cl.$^7$ ............... A01H 5/00; A01H 5/10; A01H 1/04; A01H 4/00; C12N 5/04

(52) U.S. Cl. ............ 800/320.1; 800/260; 800/271; 800/274; 800/275; 800/298; 435/410; 435/412; 435/424; 435/430

(58) Field of Search .................... 800/320.1, 298, 800/260, 271, 274, 275; 435/410, 412, 424, 430

(56) References Cited

U.S. PATENT DOCUMENTS 5,824,854   10/1998   Bergquist .

*Primary Examiner*—Gary Benzion
*Assistant Examiner*—Melissa L. Kimball
(74) *Attorney, Agent, or Firm*—Bullwinkel Partners, Ltd.

(57) ABSTRACT

A hybrid corn line having the designation P724, produced by crossing the inbred Q×47 with the progeny of the cross between proprietary inbred Z×23 and synthetic P22.1. P724 imparts a high oil level in the grain of certain male sterile hybrids when used as a pollinator. P724 is characterized by good plant vigor, including seedling vigor in cold soil tests, and gives higher test weight in TopCross® Grain than other pollinators of similar oil levels. P724 has shown excellent productivity in TC Blend® Seed Products of medium season adaptability. This invention thus relates to the seeds, plants and plant parts of P724 and its components, to plants regenerated from tissue culture of the plants of P724, to a method of producing P724, and to a method for producing high oil grain using P724 as a pollinator.

16 Claims, No Drawings

CORN HYBRID P724

FIELD OF THE INVENTION

This invention is in the field of maize breeding. Specifically, this invention relates to a novel corn hybrid having the designation P724.

BACKGROUND OF THE INVENTION

Principles of conventional plant breeding

Most of the commercial corn produced in the United States is produced from hybrid seed. The production of hybrid seed first requires the development of elite corn inbred lines that possess good combining ability to produce agronomically superior hybrids. The majority of hybrid seed produced in the United States is of the single cross type, wherein two inbred lines are intermated, or crossed, to produce what is termed seed of an $F_1$ single cross hybrid. This seed is then sold to commercial grain growers who plant the seed and harvest the second generation, or $F_2$ grain, for use on farm or for commercial sale.

The production of conventional single cross hybrid seed involves controlling the direction of pollination from one inbred to the other to assure the production of predominantly hybrid (cross pollinated) seed. Typically, directed pollination is accomplished by interplanting separate rows of female corn plants with male corn plants. The female corn plants that are male sterile may be produced by genetic mechanisms which render the corn tassel or pollen nonfunctional or by detasseling the plants in the field.

The development of corn hybrids requires the development of homozygous inbred lines, the crossing of these lines, and the evaluation of the crosses. Pedigree breeding, backcross conversion and recurrent selection breeding methods are used to develop the inbred lines from breeding populations. These breeding methods combine desirable traits from two or more inbred lines or various broad-based populations into breeding pools from which new inbred lines are developed by inbreeding or random mating and selection of desired phenotypes. The new inbreds are crossed with other inbreds and the resulting hybrids are evaluated to determine which have commercial value and agronomic usefulness.

The objective of typical plant breeding is to develop a hybrid with desirable traits such as resistance to diseases and insects, herbicide tolerance, tolerance to heat and drought, reduction of time to crop maturity, and improved agronomic quality. Because many crops are harvested mechanically, uniformity of plant characteristics such as germination time, stand establishment, growth rate, and fruit/seed size are also desirable.

The problem with conventional breeding techniques is that there are several grain quality traits, such as high oil concentration, that cannot readily be obtained in a high-yielding single cross hybrid. One solution to this problem has been proposed by Bergquist et al. in U.S. Pat. Nos. 5,704,160 and 5,706,603, incorporated herein by reference. A primary aspect of this method, known as the TOPCROSS® Grain Production System is the interplanting of a pollinator corn plant possessing the characteristics for significantly increasing oil level in the resulting grain, with a male sterile hybrid corn plant. The resulting grain possesses an oil concentration much higher than would be expected for self- or cross- pollination of the fertile version of the hybrid corn plant.

In practice, the seed of the pollinator with improved grain quality traits is blended in small amounts with seed of an elite male sterile grain parent hybrid, but with sufficient pollinator seed to permit abundant pollen production for fertilization of the male sterile grain parent hybrid. The relatively low ratio of pollinator seed to male sterile grain parent seed (less than one pollinator plant to every three grain parent plants) takes advantage of the higher grain yield potential of the elite grain parent hybrid while assuring a sufficient population of pollinator plants to pollinate the male sterile grain parent plants.

Critical to the success of the TOPCROSS® Grain Production System is the use of a pollinator capable of enhancing the grain quality traits of the $F_1$ grain. P724 was developed for this purpose. The present invention, when used as a pollinator, imparts high oil concentration to the resulting $F_1$ grain without significant loss of yield.

According to the invention, there is provided a novel corn hybrid, designated P724, that when used to pollinate an elite male sterile hybrid grain parent, produces commercial grain exhibiting improved quality grain traits, including high oil. P724 is a medium flowering hybrid, broadly adapted to the corn growing areas of the Central United States. Grain from P724 has expressed high oil, and good test weight.

The invention thus relates to the seeds, plants and plant parts of P724; to tissue culture comprising regenerable cells of a plant part of P724; to plants regenerated from regenerable cells of the tissue culture of P724; to corn plants having substantially all the phenotypic, genotypic and/or physiological characteristics of P724; to the method of producing P724; to grain or seed produced by crossing P724 with a different corn plant wherein the resulting progeny have one-half the nuclear genotype of P724; to seed blends of P724 and male sterile corn hybrids; to a method of producing high oil grain using P724 as a pollinator in a TC BLEND® Seed Product; and to corn plants produced or derived from P724 seed wherein the corn plants have the ability to impart high oil or other grain quality traits to the F1 grain when these P724-derivatives are used in the TOPCROSS® Grain Production System.

DEFINITIONS

In the description that follows, a number of terms are used. In order to provide a clear and consistent understanding of the specification and claims, including the scope to be given such terms, the following definitions are provided:

Combining Ability. The ability of a genetic strain, when crossed with another strain, to produce a high proportion of desirable individuals.

Endosperm. The nutritive tissue formed within the embryo sac in seed plants. It commonly arises following the fertilization of the diploid polar nucleus by one male sperm.

Express. To manifest a genetic character trait.

$F_1$. The first generation of a cross.

$F_2$. The second filial generation obtained by self-fertilization or crossing inter se of $F_1$ individuals. Subsequent generations are $F_3$, $F_4$, $F_5$, etc.

Genotype. The fundamental genetic constitution of an organism.

Grain. Mature corn kernels produced by commercial growers for purposes other than growing or reproducing the species.

Grain Parent. Male sterile, elite hybrid that comprises a large majority of the plants in the TOPCROSS® Grain Production System.

Grain Quality Trait. Any attribute of grain that is of commercial value. Such traits relate to the intermediate or final use of grain and include but are not limited to the quantity or quality of oil, protein, starch, pigmentation, and fiber found in corn grain. Such traits also encompass physical attributes of the grain itself, such as grain texture, size, or hardness, among others. Certain of these compositional or physical attributes of grain correlate with functional attributes as well which are of commercial importance, such as susceptibility to breakage and spoilage, among others.

Homozygous. A genetic condition existing when identical alleles reside at corresponding loci on homologous chromosomes.

Hybrid. (1) The progeny of a cross fertilization between parents belonging to different genotypes. (2) The first generation offspring of a cross between two individuals differing in one or more genes. (3) A hybrid is the result of a cross between two or more components.

Inbred or Inbred Line. A substantially homozygous individual, variety or line produced by continued inbreeding. In plant breeding a nearly homozygous line usually originates by continued self-fertilization, accompanied by selection.

Kernel. The corn caryopsis comprising a mature embryo and endosperm which are products of double fertilization.

Line. (1) A group of individuals from a common ancestry. (2) A narrowly defined group that is a variety.

Male Sterile. A condition in which pollen is substantially absent or non-functional in flowering plants.

Percent Oil. The oil concentration of a corn kernel, typically determined at 0% moisture.

Phenotype. (1) Physical or external appearance of an organism as contrasted with its genetic constitution (=genotype); (2) a group of organisms with similar physical or external makeup; (3) the observed character of an individual without reference to its genetic nature.

Pollen Grain. A microspore in flowering plants that germinates to form the male gametophyte which contains three haploid nuclei. One of these fertilizes the ovum, a second fuses with the two polar nuclei to form the triploid endosperm, and the third degenerates once double fertilization has been accomplished.

Pollinators. Male fertile corn plants used to pollinate male sterile hybrid corn plants in order to produce a Grain Quality Trait in the resulting F1 grain.

Population. In genetics, a community of individuals which share a common gene pool.

Seed. Mature corn kernels produced for the purpose of propagating the species.

Single Cross. A cross between two different genotypes, each of which may be an inbred or synthetic.

Synthetic (Population). A genetically heterogeneous collection of plants of known ancestry created by the intermating of any combination of inbreds, hybrids, varieties, populations, races or other synthetics.

Synthetic Hybrid. A hybrid in which one or more genotypes used to make the hybrid is a synthetic.

TC BLEND®. A registered trademark of E.I. du Pont de Nemours and Company for a physical mixture of two or more types of seed utilized in the TOPCROSS® Grain Production System.

TOPCROSS®. A registered trademark of E.I. du Pont de Nemours and Company for the TOPCROSS® Grain Production System.

DETAILED DESCRIPTION OF THE INVENTION

P724 is a high oil hybrid having superior agronomic characteristics and the ability to impart desirable grain quality traits to grain when used as a pollinator in the TOPCROSS® Grain Production System. P724 is adapted over a wide area of the Central regions of the U.S. corn belt. P724 can be used advantageously in TC BLEND® Seed Corn Products with grain parents from approximately 105–115 relative maturity.

P724 is a high oil hybrid having superior agronomic characteristics and the ability to impart desirable grain quality traits to grain when used as a pollinator in the TOPCROSS® Grain Production System. P724 is adapted over a wide area of the Central regions of the U.S. corn belt. P724 can be used advantageously in TC BLEND® Seed Corn Products with grain parents from approximately 105–115 relative maturity.

P724 is produced by crossing the proprietary corn inbred line Qx47 with progeny of the cross between the synthetic P22.1 and the proprietary inbred Zx23. Either Qx47 or the progeny of the P22.1xZx23 cross may be used as the female parent. All three of the parent lines for P724 have large, highly branched tassels.

Although P724's primary use would be as a pollinator in the TOPCROSS® Grain Production System with blends of medium maturing corn hybrid male sterile grain parents, it is also an acceptable parent to be crossed with other high oil pollinators to develop derived pollinators, for example by crossing to earlier or later pollinators for expanding the use of its genetics to wider maturity grain parents.

Comparison of P724 to Synthetic Hybrid LP57.1 and Synthetic P22.1

LP57.1 is a synthetic hybrid described in U.S. Pat. No. 5,824,854. P22.1 is a pollinator used in commercial TC Blend® Seed Corn Products. As shown in Table 1, the timing and duration of P724 flowering is very similar to P22.1 and about 1.5 days earlier to flower than LP57.1.

TABLE 1

Average of 1998–1999 P22.1, LP57.1 and P724
Flowering Observations on the Number of Days from Planting
to 10%, 50% and 90% of the Plants Shedding Pollen.
(1998: 21 locations; 1999: 28 locations;
2 replicates/location)

| Pollinator | 10% Shedding | 50% Shedding | 90% Shedding |
| --- | --- | --- | --- |
| P22.1 | 63.7 | 66.0 | 68.4 |
| LP57.1 | 65.2 | 67.5 | 69.5 |
| P724 | 63.5 | 66.0 | 68.4 |

When used as a pollinator, P724 produces kernels with an oil concentration greater than that of grain produced using P22.1 as the pollinator and about the same as that of grain using LP57.1 as the pollinator (see Table 4 in the Examples section below). The test weight of grain from P724 TC BLEND® Seed Corn Products is greater than that of grain from TC BLEND® Seed Products using LP57.1 as the pollinator (see Table 4 and Table 7). Furthermore, P724 may have improved plant vigor over P22.1 and LP57.1, as suggested by cold soil germination tests (see Table 2) and yield measurements on the pollinator plants themselves (see Table 3).

TABLE 2

1999 Field Emergence Observations, Williamsburg IA,
With a Very Early Planting Date (March 31, 1999)
Providing Cold Soil Conditions (3 replicates)

| Pollinator | Emergence |
| --- | --- |
| P22.1 | 38% |
| LP57.1 | 45% |
| P724 | 53% |

TABLE 3

1998 Yield Trial Results, Pollinators per se,
Grown in 2-row x 19 ft. Plots
in Three Midwest Locations
(3 replicates/location)

| Pollinator | Yield (bu/A) | Harvest Moisture (%) |
| --- | --- | --- |
| P22.1* | 91 | 19.6 |
| LP57.1 | 93 | 18.3 |
| P724 | 144 | 20.7 |

*P22.1 data from 2 locations, yield too low to measure at third location.

EXAMPLES OF USING P724 AS A POLLINATOR

Strip test trials were conducted by Holden's Foundation Seeds, L.L.C. in the summer of 1998 to compare the characteristics of grain produced from various hybrids rendered male sterile and pollinated by P724, P22.1 and LP57.1 respectively with the characteristics of grain produced from the self-pollination of the same hybrids in their fertile state and not pollinated by P724. As Table 4 shows, the average oil concentration of the TopCross® Grain produced using P724 as a pollinator was 3.2 percentage points higher on a dry basis than the average oil concentration of grain from the corresponding fertile hybrids. Grain moisture at harvest was 0.6 percentage points higher, test weight was 1.8 lb/bu lower, and protein was 0.1 percentage points higher in the TopCross® Grain produced using P724 as a pollinator compared to the grain from the corresponding fertile hybrids.

TABLE 4

1998 TOPCROSS ® Grain Production System Strip Test Results Using
P724, P22.1 and LP57.1 as Pollinators
Across a Range of Hybrid Grain Parents
Absolute Increase or Decrease Over the Mean Value for Grain
Produced from the Self- and Sib-pollinated Grain Parents

| Pollinator | Grain Moisture at Harvest (%) | Test Weight (lb/bu) | Oil Concentration | Protein Concentration |
| --- | --- | --- | --- | --- |
| | | | (% at 0% moisture) | |
| P724 | +0.6 | −1.8 | +3.2 | +0.1 |
| P22.1 | +0.5 | −0.8 | +2.7 | +0.1 |
| LP57.1 | +0.2 | −2.1 | +3.1 | +0.4 |

Table 5 presents 1998 TopCross® strip test data for a single grain parent hybrid (LH198SDms×LH185) pollinated by P724 at a number of locations. As Table 5 shows, the average level of oil in TopCross® Grain arising from the grain parent LH198SDms×LH185 pollinated by P724 at thirteen locations was 7.2%.

TABLE 5

1998 Strip Test Data Using
(LH198SDms x LH185) with P724

| | Grain Yield bu/acre | Grain Moisture at Harvest % | Test Weight lb/bu | Oil | Protein | Starch |
| --- | --- | --- | --- | --- | --- | --- |
| | | | | % at 0% moisture | | |
| | 168 | 18.4 | 55.5 | 7.2 | 8.4 | 68.3 |
| Number of locations | 14 | 14 | 12 | 13 | 13 | 13 |

Table 6 presents 1998 strip test data for the grain parent hybrid (LH198SDms×LH185) pollinated by P724 compared to data for the fertile check (LH198×LH185) averaged over four locations. Grain arising on the male sterile grain parent (LH198SDms×LH185) pollinated by P724 exhibited, on average, 7.6% oil and 8.4% protein at 0% moisture. Grain arising on the grain parent fertile check exhibited, on average, only 4.4% oil and 8.2% protein. Thus the oil concentration in the grain produced using the P724 pollinator was 3.2 percentage points, or 73% higher than that in the grain arising on the grain parent check when pollinated by itself.

TABLE 6

1998 TOPCROSS ® Grain Production
System Strip Test Data
Averaged Over Four Locations

| | Oil (%) | Protein (%) |
| --- | --- | --- |
| Grain Parent Fertile Check (GP) (LH198 x LH185) | 4.4 | 8.2 |
| High Oil Corn Grain ((LH198SDms x LH185) pollinated by P724) | 7.6 | 8.4 |
| High Oil Corn Grain as % of GP | 173 | 102 |

Similar results were obtained in 1999 tests. As Table 7 shows, the oil concentration in the grain arising from a range of grain parents pollinated by P724 was 2.8 percentage points higher than the oil concentration in the grain arising from the self-pollinated fertile checks.

TABLE 7

1999 TOPCROSS ® Grain Production System Strip Test Results Using
P724 and LP57.1 as Pollinators Across a
Range of Hybrid Grain Parents
Absolute Increase or Decrease Over the Mean Value for Grain
Produced from the Self- and Sib-pollinated Grain Parents

| Pollinator | Grain Moisture at Harvest (%) | Test Weight (lbs/bu) | Oil concentration (%) | Protein Content (%) |
| --- | --- | --- | --- | --- |
| P724 | +0.7 | −1.3 | +2.8 | +0.8 |
| LP57.1 | +0.5 | −2.4 | +2.9 | +0.3 |

DEPOSIT INFORMATION

Applicant has made available to the public without restriction a deposit of at least 2500 seeds of maize hybrid P724 with the American Type Culture Collection (ATCC), Rockville, Md. 20852, ATCC Deposit No. PTA-2976. The seed deposited with the ATCC was taken from the same deposit maintained by Holden's Foundation Seeds, L.L.C., 503 S. Maplewood Ave., P.O. Box 839, Williamsburg, Iowa 52361 since prior to the filing date of this application. The deposit will be maintained in the ATCC depository, which is a public depository, for a period of 30 years, or 5 years after the most recent request, or for the enforceable life of the patent, whichever is longer, and will be replaced if it becomes nonviable during that period.

Although the foregoing invention has been described in some detail by way of illustration and examples for purposes of clarity and understanding, it will be obvious that certain modifications and alternative embodiments of the invention are contemplated which do not depart from the spirit and scope of the invention as defined by the foregoing teachings and appended claims.

What is claimed is:

1. A hybrid corn line designated P724, for which a representative sample of seeds has been deposited under ATCC Accession No. PTA-2976.

2. A hybrid corn seed designated P724, a representative sample of which has been deposited with the ATCC under Accession No. PTA-2976.

3. A hybrid corn plant produced by the seed of claim 2.

4. Pollen of the hybrid corn plant of claim 3.

5. A tissue culture comprising regenerable cells of the hybrid corn plant of claim 3.

6. A corn plant regenerated from regenerable cells of the tissue culture of claim 5.

7. A corn plant having substantially all the morphological and physiological characteristics of the hybrid corn plant of claim 3.

8. A corn plant having all the phenotypic, genotypic and physiological characteristics of the hybrid corn plant of claim 3.

9. A method for producing a hybrid corn seed designated P724 and having ATCC Accession No. PTA-2976 comprising the steps of:
   a) planting in pollinating proximity seeds of corn lines Q×47, ATCC Accession No. PTA-2973, and progeny of a cross between synthetic P22.1 and inbred Z×23, ATCC Accession No. PTA-2979;
   b) cultivating corn plants resulting from the planting until the time of flowering;
   c) emasculating the flowers of the plants of either inbred line Q×47 or the progeny of the cross between synthetic P22.1 and inbred Z×23;
   d) allowing cross pollination to occur between the inbred lines; and
   e) harvesting seeds produced on the emasculated plants.

10. Grain produced by crossing a hybrid corn plant according to claim 3 with another, different corn plant.

11. Seed produced by crossing a hybrid corn plant according to claim 3 with another, different corn plant.

12. A seed corn blend comprising a mixture of male sterile hybrid corn seed and the hybrid corn seed of claim 2.

13. Corn grain produced by the process of:
   (a) planting, in pollinating proximity, the hybrid corn seed of claim 2 and seeds of a male sterile corn hybrid;
   (b) cultivating corn plants resulting from the planting;
   (c) allowing the P724 corn plants to pollinate the male sterile hybrid corn plants; and
   (d) harvesting the resulting corn grain from all plants.

14. A corn plant produced from a seed of claim 2 and having the ability to impart desirable grain quality traits to grain when used as a pollinator plant in the TOPCROSS® Grain Production System.

15. A corn plant produced from a seed of claim 2 having the ability to impart a high oil level to grain when used as a pollinator plant in the TOPCROSS® Grain Production System.

16. A corn plant derived from a seed of claim 2 and retaining the ability to impart a high oil level to grain when used as a pollinator in the TOPCROSS® Grain Production System.

* * * * *

UNITED STATES PATENT AND TRADEMARK OFFICE
CERTIFICATE OF CORRECTION

| | |
|---|---|
| PATENT NO. | : 6,284,955 B1 |
| DATED | : September 4, 2001 |
| INVENTOR(S) | : Marshall et al. |

It is certified that error appears in the above-identified patent and that said Letters Patent is hereby corrected as shown below:

<u>Title page,</u>
ABSTRACT,
Line 2, replace "QX47" with -- Qx47 --,
Line 3, replace "ZX23" with -- Zx23 --.

<u>Column 4,</u>
Line 19, replace "QX47" with -- Qx47 --,
Line 20, replace "ZX23" with -- Zx23 -- and replace "QX47" with -- Qx47 --,
Line 21, replace "ZX23" with -- Zx23 --.

<u>Claim 9,</u>
Replace "QX47" with -- Qx47 -- (both occurrences), and replace "ZX23" with -- Zx23 -- (both occurrences).

Signed and Sealed this

Twelfth Day of March, 2002

JAMES E. ROGAN
*Director of the United States Patent and Trademark Office*

*Attest:*

*Attesting Officer*